United States Patent
Yamasaki et al.

(10) Patent No.: US 10,849,596 B2
(45) Date of Patent: Dec. 1, 2020

(54) PIEZOELECTRIC ELEMENT, ULTRASONIC PROBE, ULTRASONIC MEASUREMENT DEVICE, AND MANUFACTURING METHOD OF PIEZOELECTRIC ELEMENT

(71) Applicant: SEIKO EPSON CORPORATION, Tokyo (JP)

(72) Inventors: Sayaka Yamasaki, Suwa (JP); Hiroaki Tamura, Shimosuwa-machi (JP)

(73) Assignee: SEIKO EPSON CORPORATION, Tokyo (JP)

( * ) Notice: Subject to any disclaimer, the term of this patent is extended or adjusted under 35 U.S.C. 154(b) by 1065 days.

(21) Appl. No.: 15/341,154

(22) Filed: Nov. 2, 2016

(65) Prior Publication Data

US 2017/0119351 A1    May 4, 2017

(30) Foreign Application Priority Data

Nov. 4, 2015  (JP) .................... 2015-216383

(51) Int. Cl.
*A61B 8/00* (2006.01)
*H01L 41/08* (2006.01)
(Continued)

(52) U.S. Cl.
CPC .......... *A61B 8/4494* (2013.01); *A61B 8/0891* (2013.01); *A61B 8/14* (2013.01);
(Continued)

(58) Field of Classification Search
CPC .............. H01L 41/081; H01L 41/312; H01L 41/1876; H01L 41/27; A61B 8/42;
(Continued)

(56) References Cited

U.S. PATENT DOCUMENTS

2005/0168112 A1* 8/2005 Aoki ............... H01L 41/319
                                                              310/358
2006/0012648 A1* 1/2006 Ifuku ............... H01L 41/316
                                                              347/72
(Continued)

FOREIGN PATENT DOCUMENTS

JP    60-206315 A    10/1985
JP    2008-173177 A    7/2008
(Continued)

*Primary Examiner* — Bryan P Gordon
(74) *Attorney, Agent, or Firm* — Chip Law Group (57) ABSTRACT

A piezoelectric element includes: a piezoelectric body; and a vibrating plate including single crystal silicon having anisotropy having orientation with a relatively high Young's modulus and orientation with a relatively low Young's modulus (hereinafter, referred to as "low Young's modulus orientation") as a vibrating material, in which the piezoelectric body and the vibrating plate are laminated on each other so that the low Young's modulus orientation is in a direction along a high expansion and contraction direction among a direction where a degree of expansion and contraction caused according to a support structure of the piezoelectric body is relatively high (hereinafter, referred to as "high expansion and contraction direction") and a direction where a degree thereof is relatively low.

19 Claims, 9 Drawing Sheets

[ SEC B-B ]

(51) Int. Cl.
- *H01L 41/09* (2006.01)
- *H01L 41/312* (2013.01)
- *A61B 8/08* (2006.01)
- *A61B 8/14* (2006.01)
- *B06B 1/06* (2006.01)
- *H01L 41/113* (2006.01)
- *H01L 41/187* (2006.01)
- *H01L 41/27* (2013.01)

(52) U.S. Cl.
CPC .............. *A61B 8/42* (2013.01); *A61B 8/4427* (2013.01); *A61B 8/4444* (2013.01); *A61B 8/467* (2013.01); *B06B 1/0644* (2013.01); *H01L 41/081* (2013.01); *H01L 41/0805* (2013.01); *H01L 41/0933* (2013.01); *H01L 41/1132* (2013.01); *H01L 41/1876* (2013.01); *H01L 41/27* (2013.01); *H01L 41/312* (2013.01)

(58) Field of Classification Search
CPC ... A61B 8/0891; A61B 8/4444; A61B 8/4427; B60B 1/0644; B60B 1/0607
See application file for complete search history.

(56) References Cited

U.S. PATENT DOCUMENTS

| | | | |
|---|---|---|---|
| 2007/0007860 A1* | 1/2007 | Takabe | B41J 2/14233 310/324 |
| 2008/0012910 A1* | 1/2008 | Matsuda | B41J 2/1628 347/68 |
| 2011/0304405 A1* | 12/2011 | Lander | H03H 9/02448 331/158 |
| 2012/0212102 A1* | 8/2012 | Hirabayashi | A61B 17/2202 310/322 |
| 2016/0240768 A1* | 8/2016 | Fujii | H01L 41/0973 |

FOREIGN PATENT DOCUMENTS

| | | |
|---|---|---|
| JP | 2012-237673 A | 12/2012 |
| JP | 2013-078877 A | 5/2013 |
| JP | 2014-102355 A | 6/2014 |
| JP | 2015-162813 A | 9/2015 |

* cited by examiner

[ SEC A-A ]

FIG. 4

[ SEC B-B ]

PIEZOELECTRIC ELEMENT, ULTRASONIC PROBE, ULTRASONIC MEASUREMENT DEVICE, AND MANUFACTURING METHOD OF PIEZOELECTRIC ELEMENT

BACKGROUND

1. Technical Field

The present invention relates to a piezoelectric element and the like.

2. Related Art

Biological information is measured by using an ultrasonic probe and an ultrasonic measurement device using a piezoelectric element as a transducer for ultrasonic transmitting and receiving, and vascular functions are evaluated or vascular diseases are determined. For example, JP-A-2008-173177, for example, discloses an ultrasonic probe and an ultrasonic measurement device which automatically detect vascular walls by using reflected wave signal intensity from biological tissues obtained by processing amplitude information of received ultrasonic waves and a moving velocity of biological tissues obtained by processing phase information of received ultrasonic waves.

A piezoelectric element used in the ultrasonic probe and the ultrasonic measurement device is prepared by laminating a piezoelectric body on a vibrating plate on a thin film, as disclosed in JP-A-60-206315, for example.

In a case of using a piezoelectric element as an actuator which converts electricity into physical movement (for example, vibration), high-gain performance of obtaining great movement energy with low power consumption is desired, and accordingly, it is important to increase conversion efficiency. The vibrating plate is set to be thin as one method thereof, but there is limitation on the thinning of the vibrating plate due to a restriction of a manufacturing technology and the improving measures of conversion efficiency by decreasing a thickness of the vibrating plate has reached its limit.

SUMMARY

An advantage of some aspects of the invention is to provide a new technology of improving conversion efficiency of a piezoelectric element when converting electric energy into physical movement.

A first aspect of the invention is directed to a piezoelectric element including: a piezoelectric body; and a vibrating plate including single crystal silicon having anisotropy having orientation with a relatively high Young's modulus and orientation with a relatively low Young's modulus (hereinafter, referred to as "low Young's modulus orientation") as a vibrating material, in which the piezoelectric body and the vibrating plate are laminated on each other so that the low Young's modulus orientation is in a direction along a high expansion and contraction direction among a direction where a degree of expansion and contraction caused according to a support structure of the piezoelectric body is relatively high (hereinafter, referred to as "high expansion and contraction direction") and a direction where a degree thereof is relatively low.

Although will be described later in detail, it is found that a vibrating plate prepared by setting the high expansion and contraction direction of the piezoelectric body to be along the low Young's modulus orientation of the vibrating plate has higher conversion efficiency when converting electric energy into physical movement, compared to a vibrating plate prepared along other directions. Therefore, according to the first aspect of the invention, it is possible to prepare a piezoelectric element having high conversion efficiency when converting electric energy into physical movement, even with the same thickness of the material to be cut out for a vibrating plate.

More specifically, as a second aspect of the invention, the piezoelectric element according to the first aspect of the invention may be configured such that plane orientation of the single crystal silicon may be [001] and the low Young's modulus orientation is [100] or [010].

As a third aspect of the invention, the piezoelectric element according to the first aspect of the invention may be configured such that plane orientation of the single crystal silicon is [001] and the low Young's modulus orientation is [001] or [100].

As a fourth aspect of the invention, the piezoelectric element according to the first aspect of the invention may be configured such that plane orientation of the single crystal silicon is [100] and the low Young's modulus orientation is [010] or [001].

As a fifth aspect of the invention, the piezoelectric element according to the first aspect of the invention may be configured such that plane orientation of the single crystal silicon is [110] and the low Young's modulus orientation is [−100] or [001].

As a sixth aspect of the invention, the piezoelectric element according to the first aspect of the invention may be configure such that plane orientation of the single crystal silicon is [011] and the low Young's modulus orientation is [0-10] or [100].

As a seventh aspect of the invention, the piezoelectric element according to the first aspect of the invention may be configured such that plane orientation of the single crystal silicon is [101] and the low Young's modulus orientation is [10-1] or [010].

An eighth aspect of the invention is directed to an ultrasonic probe including the piezoelectric element according to any one of the first to seventh aspects for transmission of ultrasonic waves.

According to the eighth aspect of the invention, it is possible to realize an ultrasonic probe suitable for transmission of ultrasonic waves.

A ninth aspect of the invention is directed to an ultrasonic measurement device including the ultrasonic probe according to the eighth aspect.

According to the ninth aspect of the invention, it is possible to realize an ultrasonic measurement device having higher conversion efficiency when converting electric energy into physical movement.

A tenth aspect of the invention is directed to a manufacturing method of a piezoelectric element including: cutting out a vibrating material to be used in a vibrating plate from a single crystal silicon wafer having anisotropy having orientation with a relatively high Young's modulus and orientation with a relatively low Young's modulus (hereinafter, referred to as "low Young's modulus orientation"); and laminating a piezoelectric body and the vibrating plate so that the low Young's modulus orientation is in a direction along a high expansion and contraction direction among a direction where a degree of expansion and contraction caused according to a support structure of the piezoelectric body is relatively high (hereinafter, referred to as "high expansion and contraction direction") and a direction where a degree thereof is relatively low.

According to the tenth aspect of the invention, it is possible to manufacture a piezoelectric element having operation effects of the first aspect of the invention.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

Figure 1:
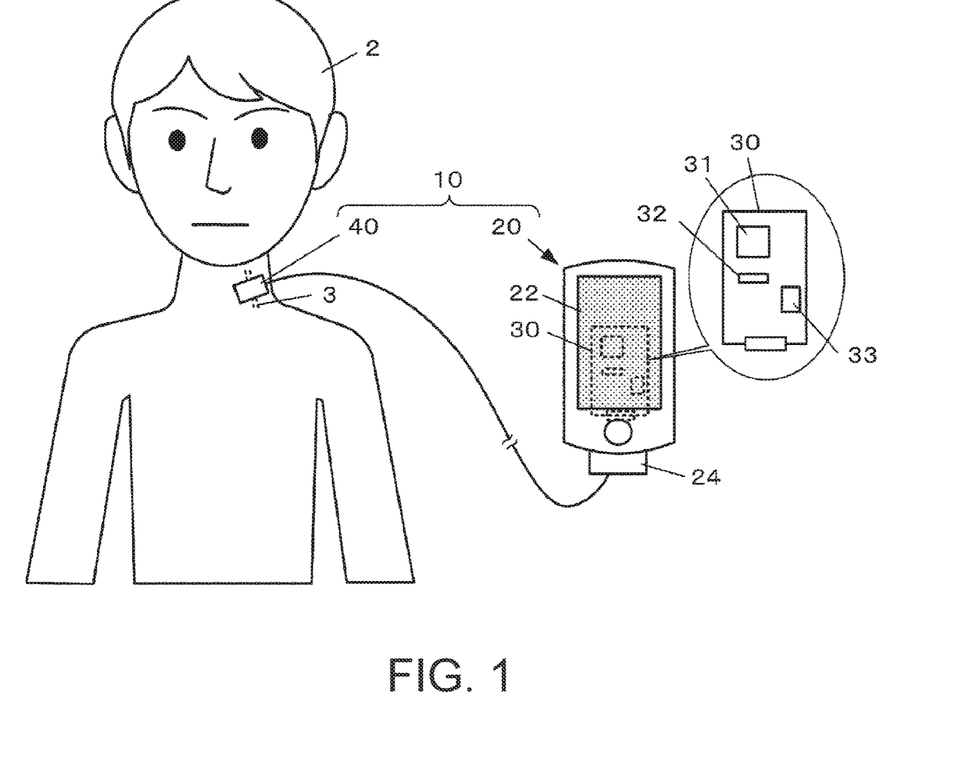
FIG. 1 is a view showing a system configuration example of an ultrasonic measurement device of a first embodiment.

FIG. 1 is a view showing a system configuration example of an ultrasonic measurement device 10 of an embodiment.

The ultrasonic measurement device 10 is a device which measures biological information of a subject 2 by transmitting ultrasonic waves to the subject 2 and measuring reflected waves. In the embodiment, vascular function information such as intima media thickness (IMT) of the carotid 3 is measured as one of the biological information items. In addition to the IMT, other vascular function information or biological information may be measured by estimating a blood vessel diameter or blood pressure from a blood vessel diameter or calculating a pulse from a change of a blood vessel diameter. A measurement target is not limited to a human.

The ultrasonic measurement device 10 includes a measurement control device 20 and an attaching-type ultrasonic probe 40.

The measurement control device 20 is a portable computer and includes a touch panel 22 which serves as both a unit for displaying an image of a measurement result or an operation information and a unit for inputting an operation, an interface circuit 24 which controls transmission and reception of a signal to and from the ultrasonic probe 40, and a control substrate 30. In addition, an embedded battery (not shown) or the like is suitably provided.

A central processing unit (CPU) 31, an IC memory 32 in addition to various integrated circuits such as application specific integrated circuit (ASIC) or a field programmable gate array (FPGA), and a communication IC 33 which realizes data communication with an external device (ultrasonic probe 40 in this embodiment) through the interface circuit 24 are mounted on the control substrate 30. The control substrate 30 realizes various functions according to the embodiment such as ultrasonic measurement by executing control programs stored in the IC memory 32 by the CPU 31 or the like.

That is, the ultrasonic measurement device 10 transmits and emits ultrasonic beams towards biological tissues from the ultrasonic probe 40 attached to the subject 2 and receives reflected waves, due to operation processes of the control substrate 30. It is possible to generate reflected wave data according to biological tissues of the subject 2 by amplifying and processing received signals of the reflected waves. The continuous measurement and the data storage of various biological information items are realized based on the reflected wave data.

Figure 2:
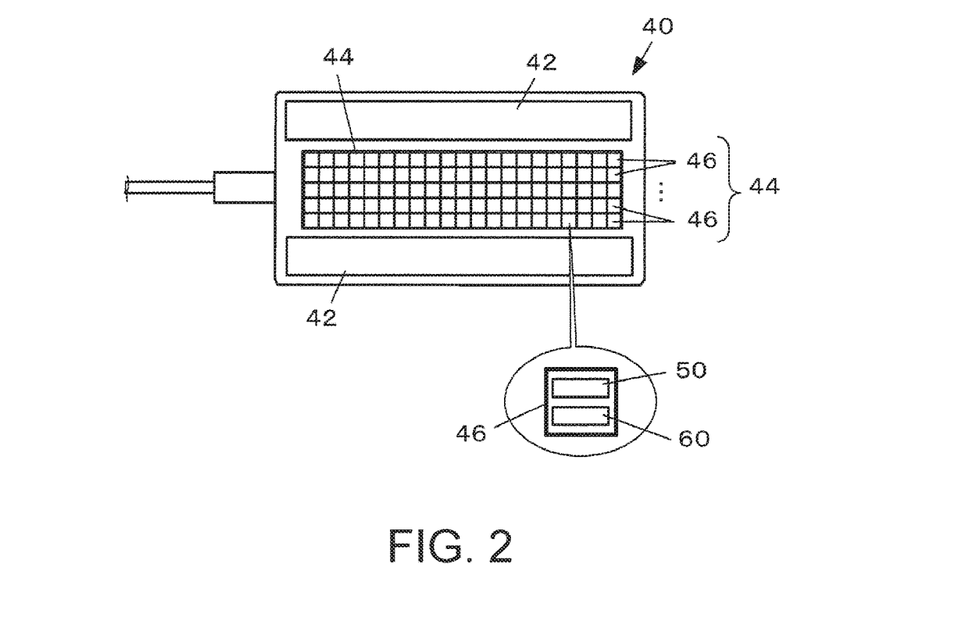
FIG. 2 is a view showing a configuration example of an ultrasonic probe of the first embodiment.

FIG. 2 is a view showing a configuration example of the ultrasonic probe 40 of the embodiment and is a view when seen from a side of the attached surface (ultrasonic transmission and reception surface) of the subject 2.

The ultrasonic probe 40 has a bonding portion 42 which detachably bonds the ultrasonic probe 40 to skin of the subject 2, and an ultrasonic sensor 44 on the attached surface side.

The ultrasonic sensor 44 is an assembly in which a plurality of ultrasonic transducers 46 are two-dimensionally arranged in a long side direction and a short side direction of the ultrasonic transmission and reception surface. The ultrasonic probe 40 is attached to skin surface of the subject 2 in a relative position in which the long side of the ultrasonic sensor 44 crosses over the carotid 3 in a short axis direction.

One ultrasonic transducer 46 includes a first piezoelectric element 50 and a second piezoelectric element 60. The first piezoelectric element 50 transmits the ultrasonic waves and the second piezoelectric element 60 receives the reflected waves.

Figure 3:
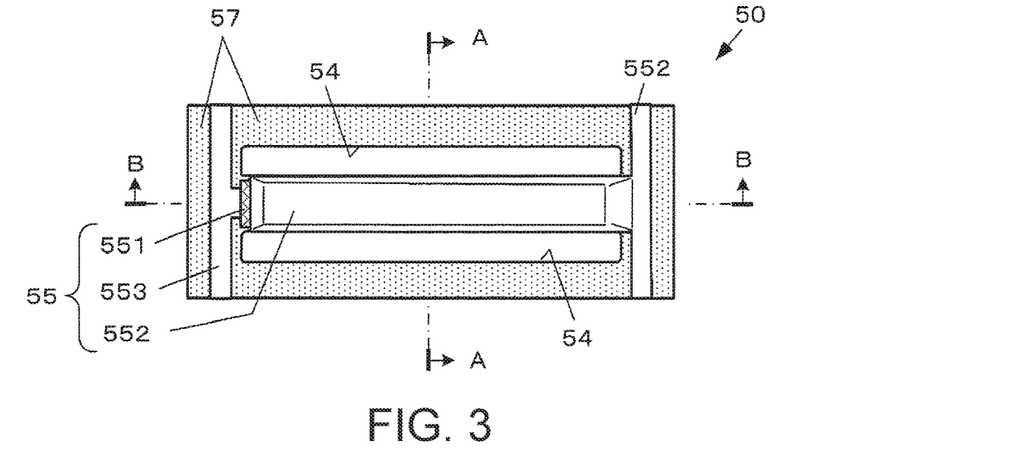
FIG. 3 is a top view showing a configuration example of a second piezoelectric element of the first embodiment.
Figure 4:
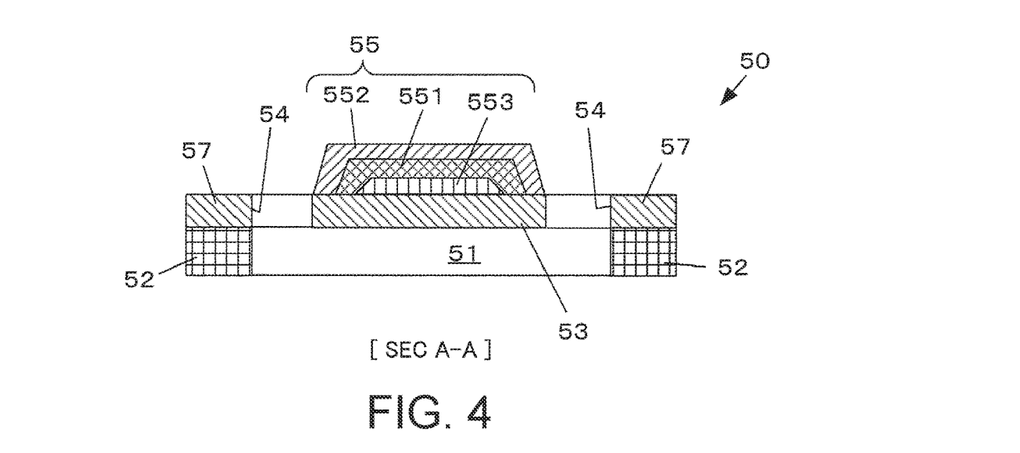
FIG. 4 is a sectional view taken along line A-A of FIG. 3.
Figure 5:
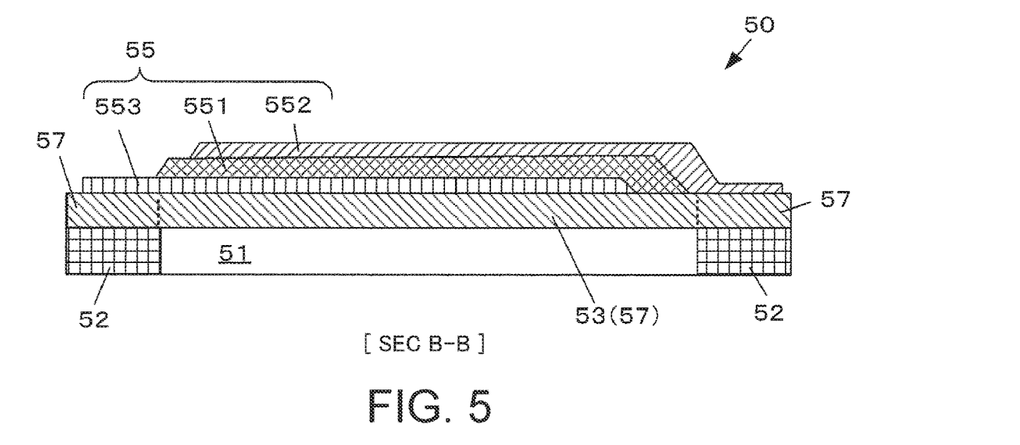
FIG. 5 is a sectional view taken along line B-B of FIG. 3.

FIG. 3 is a top view showing a configuration example of the first piezoelectric element 50 of the embodiment. FIG. 4 is a sectional view taken along line A-A of FIG. 3. FIG. 5 is a sectional view taken along line B-B of FIG. 3.

The first piezoelectric element 50 of the embodiment is an element which physically (mechanically) moves, when a voltage is applied to a piezoelectric body. More specifically, the first piezoelectric element is an element which expands and contracts in accordance with a voltage.

In the first piezoelectric element 50 of the embodiment, a thin film-shaped silicon layer 57 is bonded to an upper surface of a support substrate 52 which has a rectangular shape in a top view and where a hollow portion 51 is provided (hollow portion 51 is opened). In addition, the hollow portion 51 may be formed after forming the silicon layer 57 on the upper surface of the support substrate 52.

The silicon layer 57 includes a vibrating plate 53 having a both-ends supported beam structure (both-ends fixed support structure) which crosses the hollow portion 51. That is, the silicon layer 57 is bonded so as to cover the hollow portion 51, and two slits 54 are provided along an edge portion of the hollow portion 51 having a rectangular shape in a top view in the longitudinal direction. These two slits 54 precisely realize a bridge structure of a thin plate, that is, both-ends beams of a thin film which crosses the hollow portion 51 in the longitudinal direction.

An actuator unit 55 is laminated on the upper surface of the vibrating plate 53. The actuator unit 55 of the embodiment is configured by interposing a piezoelectric body 551 which converts electric energy into movement energy between an upper electrode 552 and a lower electrode 553. In the embodiment, as the piezoelectric body 551, piezoelectric ceramic or lead zirconate titanate (PZT) is used, but other piezoelectric materials can be suitably selected.

When the AC voltage is applied between the upper electrode 552 and the lower electrode 553, the piezoelectric body 551 and the vibrating plate 53 periodically expand and contract in a high expansion and contraction direction (in the configuration of the embodiment, longitudinal direction of the vibrating plate 53). That is, the actuator unit 55 and the vibrating plate 53 are vibrated. Accordingly, the first piezoelectric element 50 transmits ultrasonic waves to the upper side thereof (front side of FIG. 3 and upper side of FIG. 4 and FIG. 5) or the lower side thereof (rear surface side of FIG. 3 and lower side of FIG. 4 and FIG. 5).

The ultrasonic waves generated from the first piezoelectric element 50 are reflected in the body of the subject 2. The second piezoelectric element 60 receives the reflected waves and outputs a voltage in accordance with intensity of the reflected waves. The ultrasonic measurement device 10 calculates biological information by performing the operation process of the voltage by the measurement control device 20.

The conversion efficiency from the electric energy into physical movement (hereinafter, suitably and simply referred to as "conversion efficiency") obtained by the first piezoelectric element 50 is dependent on the thin thickness of the vibrating plate 53, in addition to the actuator unit 55, but there is a limitation due to a restriction of the manufacturing technology.

Therefore, in the embodiment, a material having anisotropy having different Young's modulus due to orientation is used as a thin film material for preparing the vibrating plate 53, in order to increase the conversion efficiency of the first piezoelectric element 50. The first piezoelectric element 50 is prepared so that the high expansion and contraction direction of the vibrating plate 53 is along the orientation in which the Young's modulus is relatively low (low Young's modulus orientation). The high expansion and contraction direction of the vibrating plate 53 is determined depending on the support structure of the vibrating plate 53, and in the case of this embodiment, the high expansion and contraction direction thereof is the longitudinal direction, because a structure of supporting the longitudinal shaped piezoelectric body 551 with both ends is used.

Figure 6:
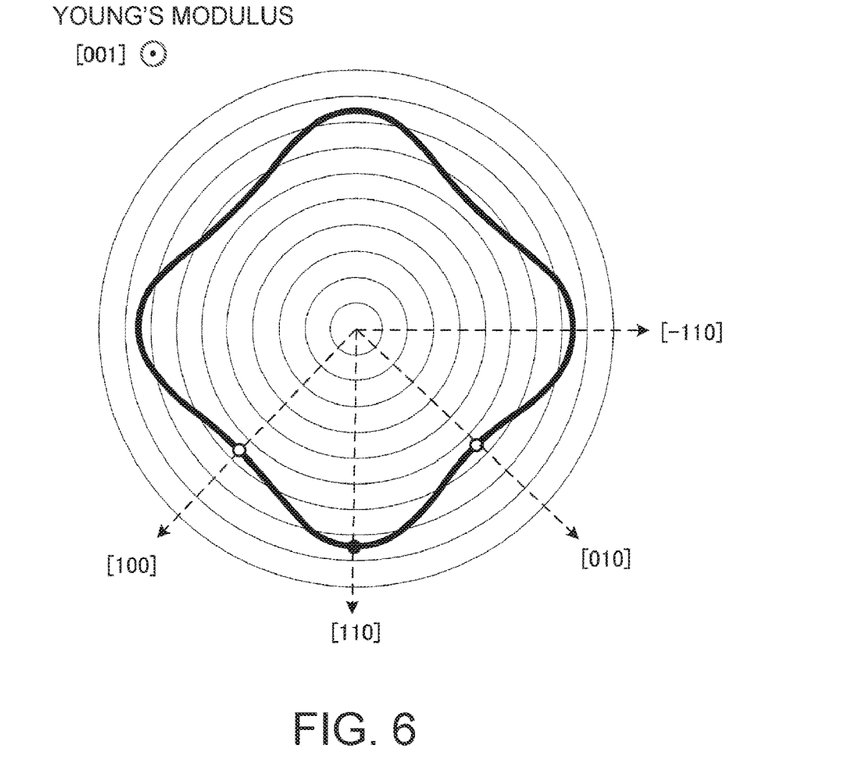
FIG. 6 is a graph showing an example of anisotropy of a Young's modulus of the [001] plane of single crystal silicon.

FIG. 6 is a graph showing an example of anisotropy of a Young's modulus of the [001] plane of single crystal silicon. A front direction of FIG. 6 is shown as plane orientation [001] and a lower side of FIG. 6 is shown as plane orientation [110].

As shown in FIG. 6, the Young's modulus of the [001] plane of the single crystal silicon has anisotropy shown with a rhombic shape in which each center of four sides is slightly recessed to the inner side. In this embodiment, the material of the vibrating plate 53 is cut out so that the longitudinal direction becomes a direction along any of the plane orientation [100] and the plane orientation [010] where the Young's modulus locally decreases.

Figure 7:
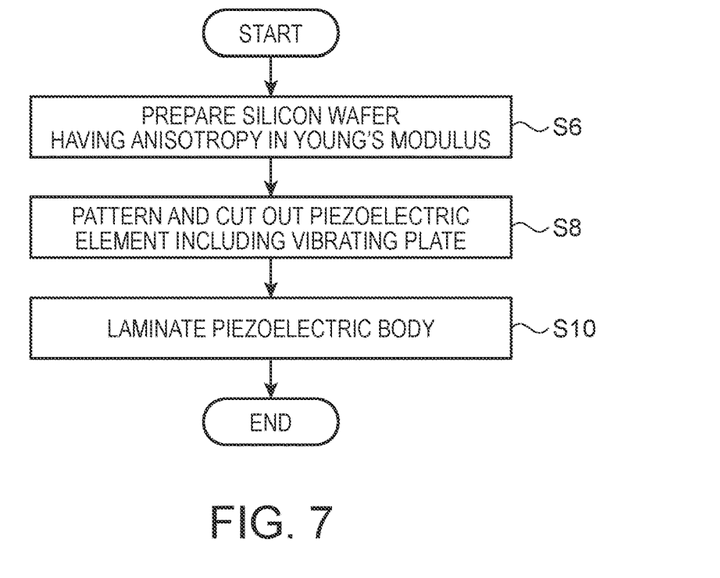
FIG. 7 is a flowchart for illustrating a manufacturing step of the second piezoelectric element of the first embodiment.

FIG. 7 is a flowchart for illustrating a manufacturing step of the first piezoelectric element 50 of the embodiment. First, in the manufacturing step of the first piezoelectric element 50 of the embodiment, a silicon wafer 7 is prepared by slicing a single crystal silicon ingot in the plane orientation where anisotropy of a Young's modulus is generated (Step S6). The silicon wafer 7 is not only prepared by slicing the single crystal silicon ingot, but may be prepared by separately purchasing the silicon wafer 7 in the [001] plane orientation.

Next, the first piezoelectric element 50 is patterned to cut out the silicon layer 57 of the first piezoelectric element 50 including a material of the vibrating plate 53, by setting the longitudinal direction of the vibrating plate 53 to be along the low Young's modulus orientation in the silicon wafer 7 (Step S8). Then, the first piezoelectric element 50 is prepared by laminating the piezoelectric body 551 including the upper electrode 552 and the lower electrode 553, and the vibrating plate 53 (Step S10).

Figure 8:
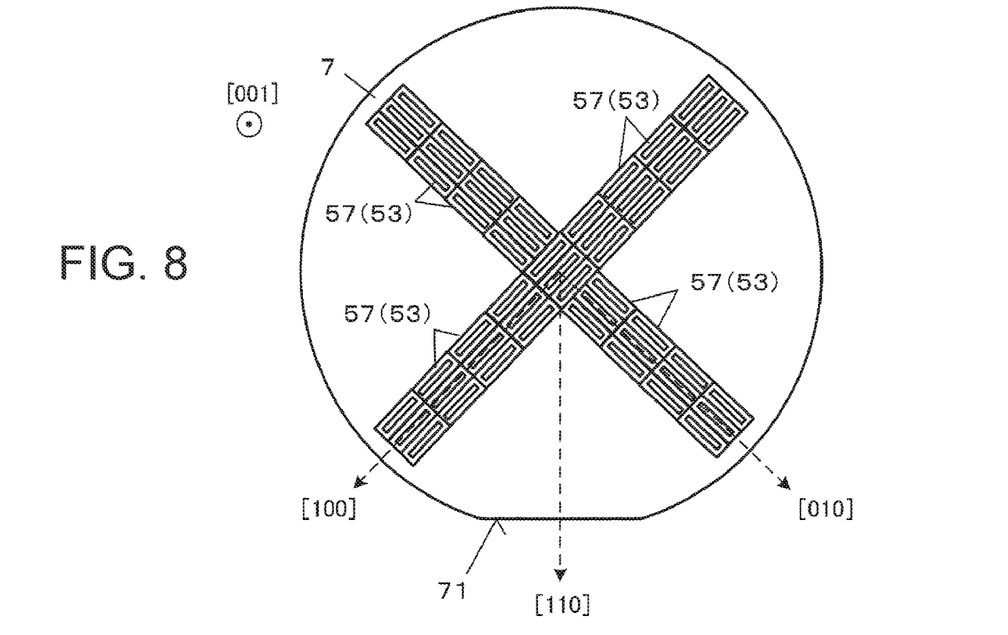
FIG. 8 is a perspective view for illustrating a positional relationship of patterning of a silicon layer and a vibrating plate of a [001]-orientated silicon wafer of the first embodiment.

FIG. 8 is a perspective view for illustrating a positional relationship of patterning of the silicon layer 57 including the vibrating plate 53 of the [001]-orientated silicon wafer 7 of the embodiment.

In FIG. 8, an orientation flat 71 is formed on the edge portions corresponding to the plane orientation [110] in the [001]-orientated silicon wafer 7. Accordingly, the silicon layer 57 of each first piezoelectric element 50 is patterned by using the orientation flat 71 as a mark. Specifically, the patterning is performed so that the longitudinal direction of the vibrating plate 53 is a direction along any of the plane orientation [100] and the plane orientation [010] where low Young's modulus orientation is obtained.

In FIG. 8, the enlarged size of silicon layer 57 used in each first piezoelectric element 50 than the actual size is shown for convenience of understanding.

Hereinabove, according to the embodiment, it is possible to realize the first piezoelectric element 50 as a high-output and energy-saving piezoelectric actuator having improved conversion efficiency, while maintaining the thickness of the vibrating plate 53.

The laminated structure of the first piezoelectric element 50 of the embodiment is used, but a configuration of further providing a thin film sheet layer on the upper surface side may be used.

Second Embodiment

Next, a second embodiment to which the invention is applied will be described.

This embodiment is basically realized in the same manner as in the first embodiment, but the plane orientation of the silicon wafer used is different and a patterning direction of the silicon layer 57 including the vibrating plate 53 is different. Hereinafter, the differences from the first embodiment will be described and the same reference numerals are used for the same constituent elements and the description thereof will be omitted.

Figure 9:
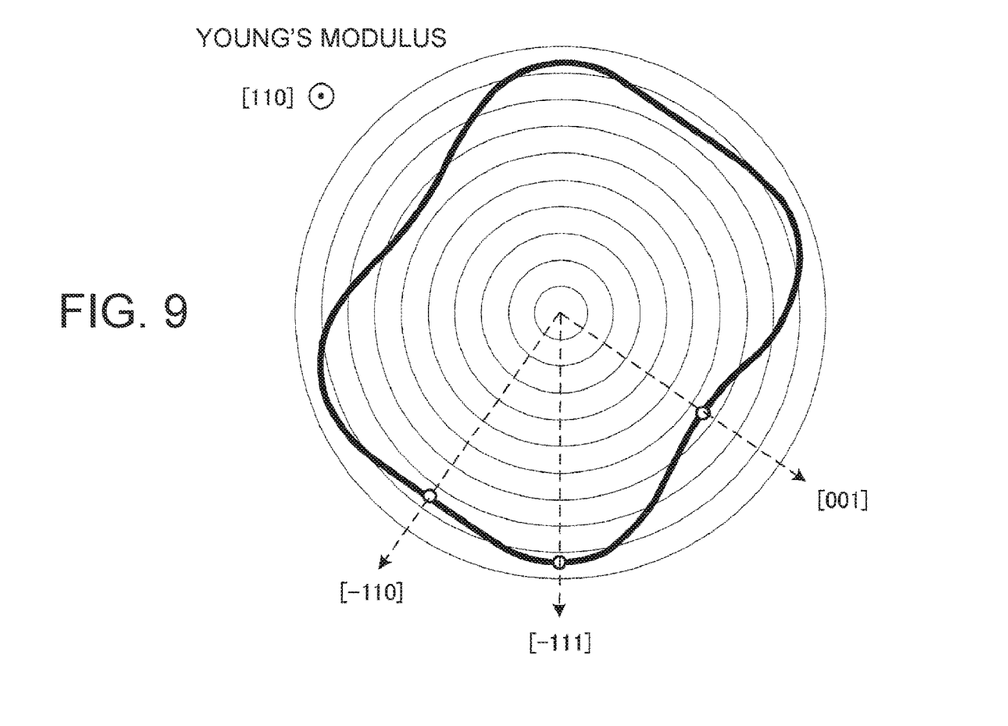
FIG. 9 is a graph showing an example of anisotropy of a Young's modulus of the [110] plane of single crystal silicon.

FIG. 9 is a graph showing an example of anisotropy of a Young's modulus of the [110] plane of single crystal silicon. A front direction of FIG. 9 is shown as plane orientation [110] and a lower side of FIG. 9 is shown as plane orientation [−111].

The Young's modulus of the [110] plane of silicon has anisotropy shown with a rhombic shape in which each center of four sides is slightly recessed to the inner side. Accordingly, in the embodiment, the silicon layer 57 including the vibrating plate 53 is cut out so that the longitudinal direction of the vibrating plate 53 is along any of the plane orientation [001] and the plane orientation [−110] where the Young's modulus locally decreases.

Figure 10:
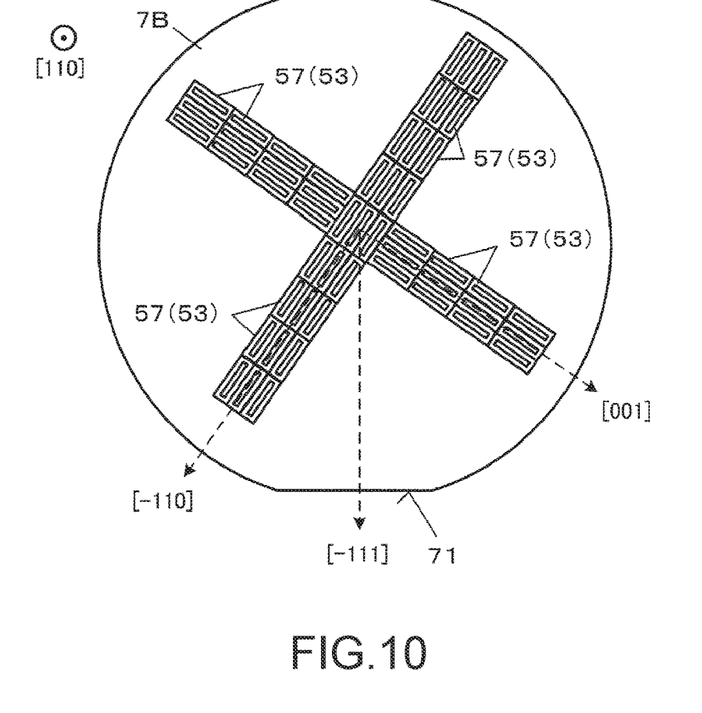
FIG. 10 is a perspective view for illustrating a positional relationship of patterning of a silicon layer and a vibrating plate of a [110]-orientated silicon wafer of a second embodiment.

FIG. 10 is a perspective view for illustrating a positional relationship of patterning of the silicon layer 57 including the vibrating plate 53 of a [110]-orientated silicon wafer 7B.

The orientation flat 71 is formed in the plane orientation [−111] in the [110]-orientated silicon wafer 7B. Accordingly, the silicon layer 57 of each first piezoelectric element 50 is patterned by using the orientation flat 71 as a reference. Specifically, the patterning is performed so that the longitudinal direction of the vibrating plate 53 is a direction along any of the plane orientation [001] and the plane orientation [−110] where low Young's modulus orientation is obtained.

Figure 11:
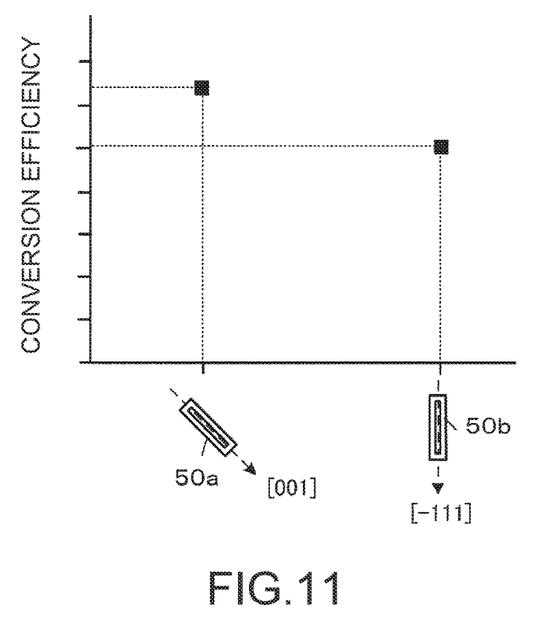
FIG. 11 is a graph of an experiment result showing a difference in conversion efficiency of 1) a second piezoelectric element prepared by setting a longitudinal direction of a vibrating plate to be along the plane orientation [001] and 2) a second piezoelectric element prepared by setting a longitudinal direction of a vibrating plate to be along the plane orientation [−111] from the [110]-oriented silicon wafer.

FIG. 11 is a graph of an experiment result showing a difference in conversion efficiency of 1) a first piezoelectric element 50a prepared by setting the longitudinal direction of a vibrating plate 53 to be along the plane orientation [001] (low Young's modulus orientation) and 2) a first piezoelectric element 50b prepared by setting the longitudinal direction of a vibrating plate 53 to be along the plane orientation [−111] (high Young's modulus orientation) from the [110]-oriented silicon wafer 7. As shown in FIG. 11, even in a case of the vibrating plate prepared from the silicon wafer 7 having the same thickness, the first piezoelectric element 50a prepared by setting the longitudinal direction to be along the plane orientation [110] (low Young's modulus orientation) has responsiveness to ultrasonic waves which is improved 1.27 times of that of the first piezoelectric element 50b prepared by setting the longitudinal direction to be along the plane orientation [−111] (high Young's modulus orientation).

In the second embodiment, it is possible to realize the first piezoelectric element 50 having improved conversion efficiency while maintaining the thickness of the vibrating plate 53, in the same manner as in the first embodiment.

Third Embodiment

Next, a third embodiment to which the invention is applied will be described.

This embodiment is basically realized in the same manner as in the first embodiment, but the structure of the first piezoelectric element 50 is different. Hereinafter, the differences from the first embodiment will be mainly described and the same reference numerals are used for the same constituent elements and the description thereof will be omitted.

Figure 12:
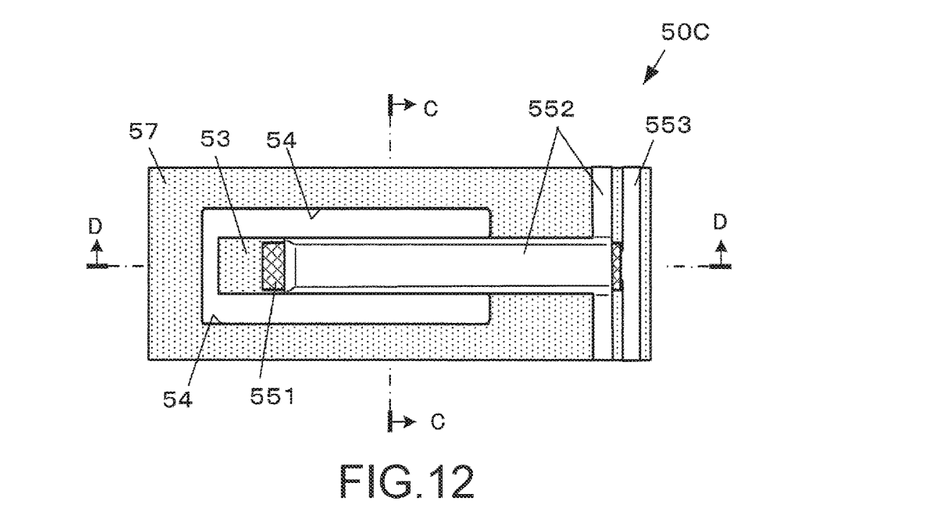
FIG. 12 is a top view showing a configuration example of a second piezoelectric element of a third embodiment.
Figure 13:
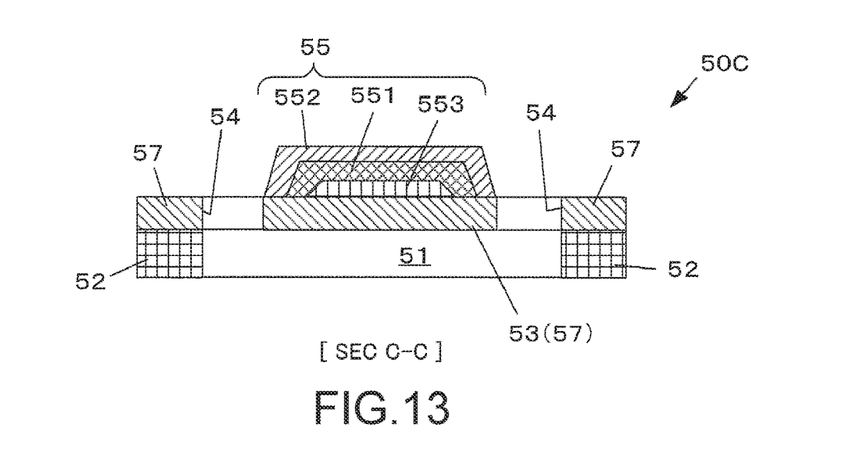
FIG. 13 is a sectional view taken along line C-C of FIG. 12.
Figure 14:
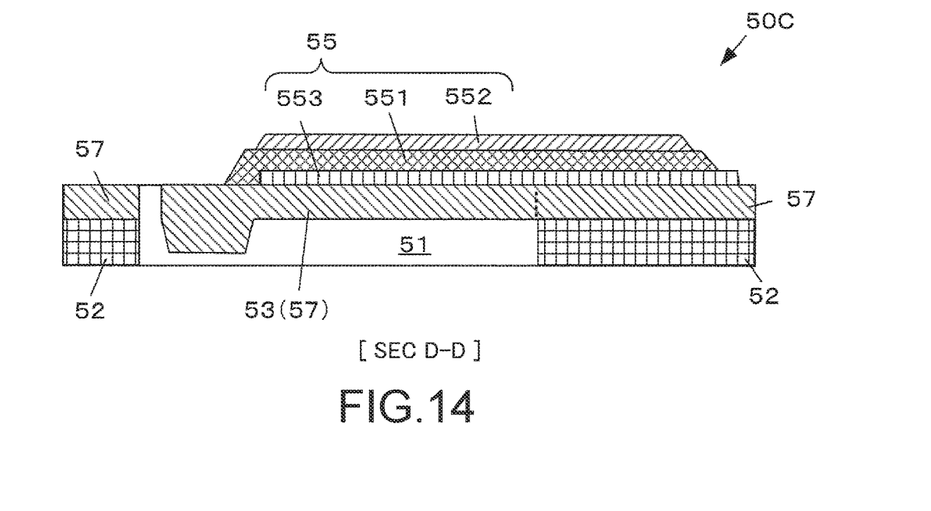
FIG. 14 is a sectional view taken along line D-D of FIG. 12.

FIG. 12 is a top view showing a configuration example of a first piezoelectric element 50C of the embodiment. FIG. 13 is a sectional view taken along line C-C of FIG. 12. FIG. 14 is a sectional view taken along line D-D of FIG. 12. In the first piezoelectric element 50C of the embodiment, a cantilever beam structure of a thin film in which the vibrating plate 53 is extended to the hollow portion 51 is formed.

The patterning of the silicon wafer 7 of the silicon layer 57 including the vibrating plate 53 is performed in the same manner as in the first embodiment or the second embodiment.

Modification Examples

Hereinabove, the embodiments to which the invention is applied have been described, but adding, omission, and modification of the constituent elements can be suitably performed.

First Example

Figure 15:
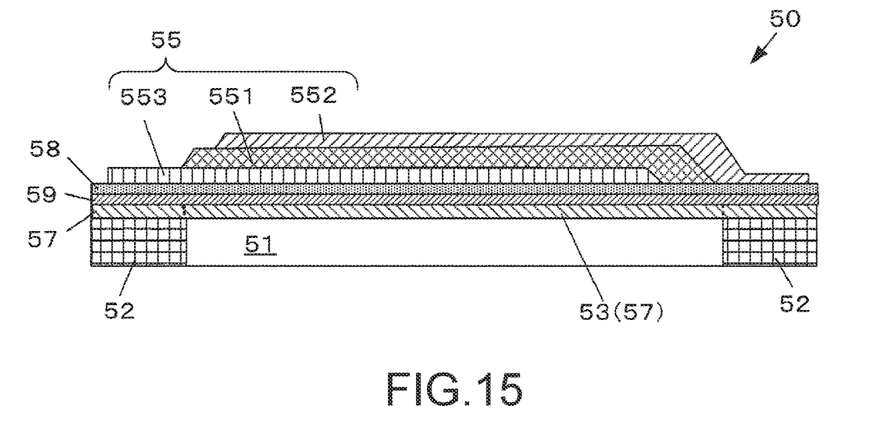
FIG. 15 is a sectional view showing a modification example of a configuration of the second piezoelectric element (first example).

For example, in the embodiments described above, the vibrating plate 53 has a single-layer structure of silicon, but as shown in a vibrating plate longitudinal direction sectional view of FIG. 15 (corresponding to FIG. 5), a multi-layer structure including a zirconia oxide layer 58 or a silicon dioxide layer 59 between the vibrating plate 53 and the actuator unit 55 may be used.

Second Example

Figure 16:
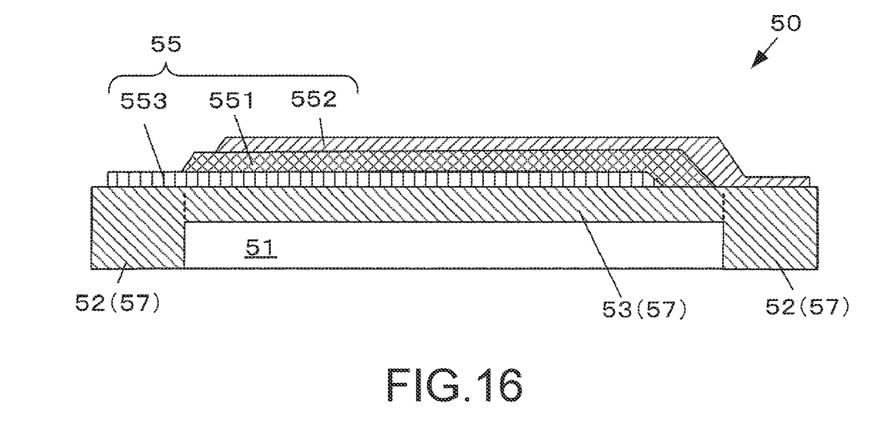
FIG. 16 is a sectional view showing a modification example of a configuration of the second piezoelectric element (second example).

In the embodiments described above, the support substrate 52 and the silicon layer 57 are separate materials, but as shown in a vibrating plate longitudinal direction sectional view of FIG. 16, the same material is used for the support substrate 52 and the silicon layer 57, and the hollow portion 51 may be prepared by etching or the like.

Third Example

Figure 17:
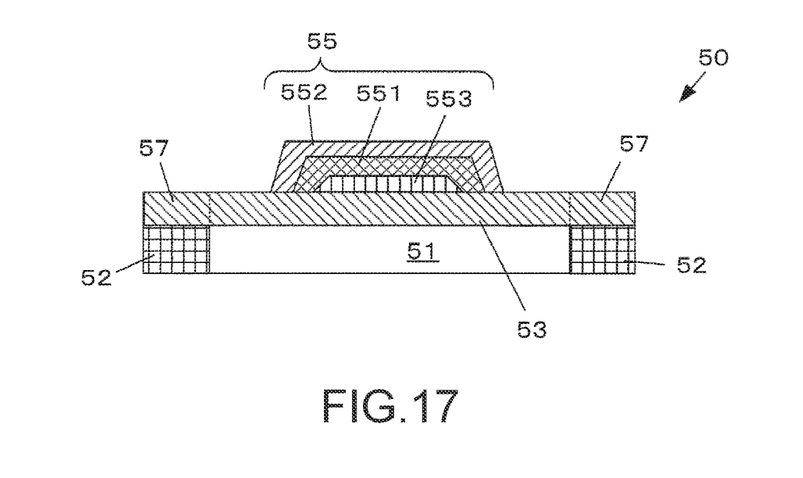
FIG. 17 is a sectional view showing a modification example of a configuration of the second piezoelectric element (third example).

In the embodiments described above, the slits 54 are provided around the vibrating plate 53, but as shown in the sectional view of FIG. 17 (corresponding to FIG. 4), the slits 54 may be omitted. For example, when the vibrating plate 53 has a rectangular shape in a top view, a support structure in which the four sides are supported by the support substrate 52 can be used. In this case, since the high expansion and contraction direction when an external force is received is set as the short direction of the vibrating plate 53 (piezoelectric body 551), the vibrating plate 53 may be prepared and laminated so that this direction is along the low Young's modulus orientation. The same can also be applied to the configurations of FIG. 15 and FIG. 16.

Fourth Example

In the embodiments described above, each ultrasonic transducer 46 includes the first piezoelectric element 50 for transmission and the second piezoelectric element 60 for reception, separately, but the first piezoelectric element 50 may also serve as a piezoelectric element for reception and the second piezoelectric element 60 may not be used.

Fifth Example

In the embodiments described above, single crystal silicon is used as the material of the vibrating plate 53, but other materials may be used as long as they are materials capable of preparing a thin plate in the crystal orientation plane having anisotropy of a Young's modulus in a deviation angle direction. For example, a material of other elements belong to the same carbon family (carbon group) of silicon such as gallium arsenide can also be used.

Sixth Example

The first embodiment can also be applied to single crystal silicon of the plane orientation [010] and single crystal silicon of the plane orientation [100].

Figure 18:
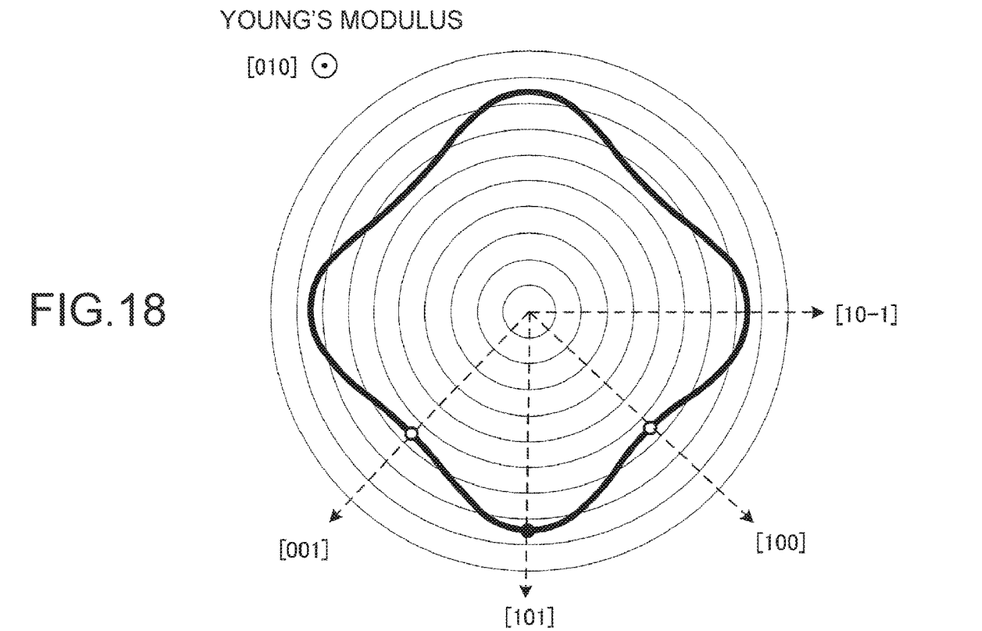
FIG. 18 is a graph showing an example of anisotropy of a Young's modulus of the [010] plane of single crystal silicon.

That is, the Young's modulus of the [010] plane of the single crystal silicon also has anisotropy, as shown in FIG. 18. Accordingly, the material of the vibrating plate 53 may be cut out so that the longitudinal direction becomes a direction along any of the plane orientation [001] and the plane orientation [100] where the Young's modulus locally decreases.

Figure 19:
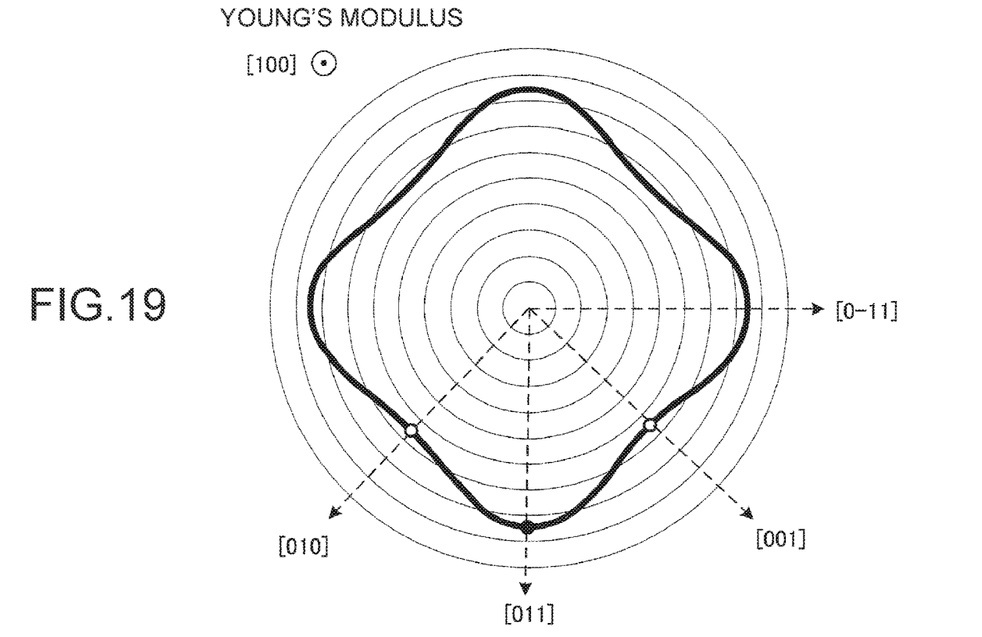
FIG. 19 is a graph showing an example of anisotropy of a Young's modulus of the [100] plane of single crystal silicon.

In the same manner as described above, the Young's modulus of the [100] plane of the single crystal silicon also has anisotropy, as shown in FIG. 19. Accordingly, the material of the vibrating plate 53 may be cut out so that the longitudinal direction becomes a direction along any of the plane orientation [010] and the plane orientation [001] where the Young's modulus locally decreases.

Seventh Example

The second embodiment can also be applied to single crystal silicon of the plane orientation [011] and single crystal silicon of the plane orientation [101].

Figure 20:
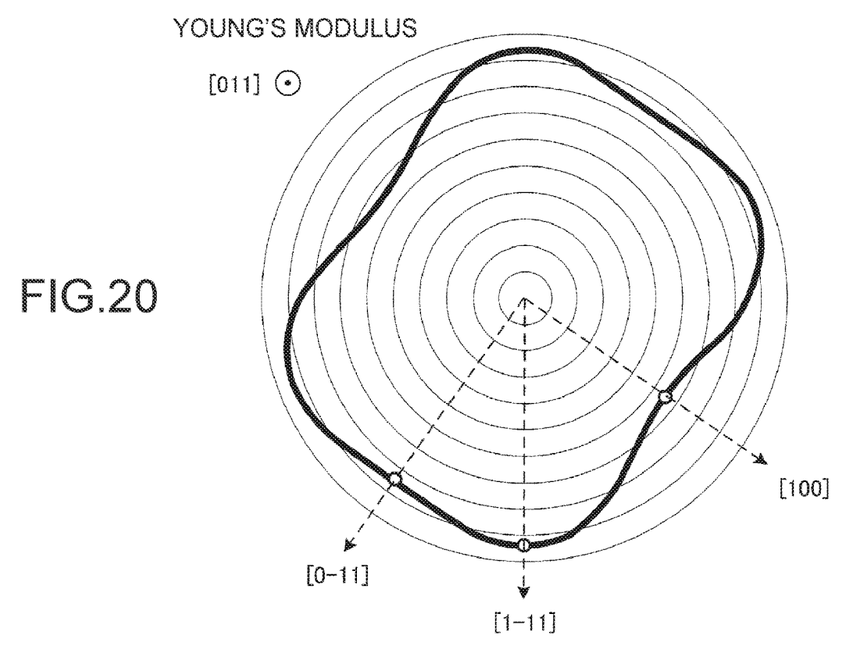
FIG. 20 is a graph showing an example of anisotropy of a Young's modulus of the [011] plane of single crystal silicon.

That is, the Young's modulus of the [011] plane of the single crystal silicon also has anisotropy, as shown in FIG. 20. Accordingly, the material of the vibrating plate 53 may be cut out so that the longitudinal direction becomes a direction along any of the plane orientation [0-11] and the plane orientation [100] where the Young's modulus locally decreases.

Figure 21:
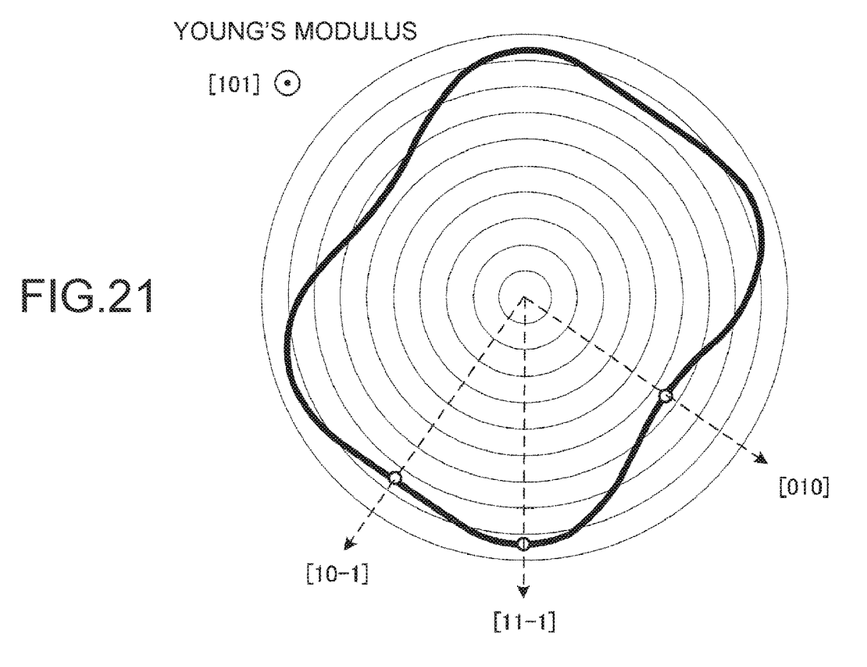
FIG. 21 is a graph showing an example of anisotropy of a Young's modulus of the [101] plane of single crystal silicon.

In the same manner as described above, the Young's modulus of the [101] plane of the single crystal silicon also has anisotropy, as shown in FIG. 21. Accordingly, the material of the vibrating plate 53 may be cut out so that the longitudinal direction becomes a direction along any of the plane orientation [10-1] and the plane orientation [010] where the Young's modulus locally decreases.

The entire disclosure of Japanese Patent Application No. 2015-216383 filed on Nov. 4, 2015 is expressly incorporated by reference herein.

What is claimed is:

1. A piezoelectric element comprising:
    a piezoelectric body; and
    a vibrating plate including single crystal silicon having anisotropy having orientation with a relatively high Young's modulus and orientation with a relatively low Young's modulus as a vibrating material,
    wherein the piezoelectric body and the vibrating plate are laminated on each other so that the low Young's modulus orientation is in a direction along a high expansion and contraction direction among a direction where a degree of expansion and contraction caused according to a support structure of the piezoelectric body is relatively high and a direction where a degree thereof is relatively low.

2. The piezoelectric element according to claim 1, wherein plane orientation of the single crystal silicon is [001] and the orientation with the relatively low Young's modulus is [100] or [010].

3. The piezoelectric element according to claim 1, wherein plane orientation of the single crystal silicon is [001] and the orientation with the relatively low Young's modulus is [001] or [100].

4. The piezoelectric element according to claim 1, wherein plane orientation of the single crystal silicon is [100] and the orientation with the relatively low Young's modulus is [010] or [001].

5. The piezoelectric element according to claim 1, wherein plane orientation of the single crystal silicon is [110] and the orientation with the relatively low Young's modulus is [-100] or [001].

6. The piezoelectric element according to claim 1, wherein plane orientation of the single crystal silicon is [011] and the orientation with the relatively low Young's modulus is [0-10] or [100].

7. The piezoelectric element according to claim 1, wherein plane orientation of the single crystal silicon is [101] and the orientation with the relatively low Young's modulus is [10-1] or [010].

8. An ultrasonic probe comprising the piezoelectric element according to claim 1 for transmission of ultrasonic waves.

9. An ultrasonic probe comprising the piezoelectric element according to claim 2 for transmission of ultrasonic waves.

10. An ultrasonic probe comprising the piezoelectric element according to claim 3 for transmission of ultrasonic waves.

11. An ultrasonic probe comprising the piezoelectric element according to claim 4 for transmission of ultrasonic waves.

12. An ultrasonic probe comprising the piezoelectric element according to claim 5 for transmission of ultrasonic waves.

13. An ultrasonic probe comprising the piezoelectric element according to claim 6 for transmission of ultrasonic waves.

14. An ultrasonic measurement device comprising the ultrasonic probe according to claim 8.

15. An ultrasonic measurement device comprising the ultrasonic probe according to claim 9.

16. An ultrasonic measurement device comprising the ultrasonic probe according to claim 10.

17. An ultrasonic measurement device comprising the ultrasonic probe according to claim 11.

18. An ultrasonic measurement device comprising the ultrasonic probe according to claim 12.

19. An ultrasonic measurement device comprising the ultrasonic probe according to claim 13.

* * * * *